United States Patent
Cook et al.

(10) Patent No.: US 11,523,801 B2
(45) Date of Patent: Dec. 13, 2022

(54) AUTOMATICALLY IDENTIFYING ANATOMICAL STRUCTURES IN MEDICAL IMAGES IN A MANNER THAT IS SENSITIVE TO THE PARTICULAR VIEW IN WHICH EACH IMAGE IS CAPTURED

(71) Applicant: EchoNous, Inc., Redmond, WA (US)

(72) Inventors: Matthew Cook, Woodinville, WA (US); Allen Lu, Seattle, WA (US)

(73) Assignee: EchoNous, Inc., Redmond, WA (US)

( * ) Notice: Subject to any disclaimer, the term of this patent is extended or adjusted under 35 U.S.C. 154(b) by 330 days.

(21) Appl. No.: 16/913,322

(22) Filed: Jun. 26, 2020

(65) Prior Publication Data

US 2021/0345992 A1 Nov. 11, 2021

Related U.S. Application Data

(60) Provisional application No. 63/022,986, filed on May 11, 2020.

(51) Int. Cl.
*A61B 8/00* (2006.01)
*G16H 30/40* (2018.01)
(Continued)

(52) U.S. Cl.
CPC ............... *A61B 8/469* (2013.01); *A61B 8/08* (2013.01); *A61B 8/14* (2013.01); *A61B 8/463* (2013.01);
(Continued)

(58) Field of Classification Search
CPC .. A61B 8/469; A61B 8/08; A61B 8/14; A61B 8/463; A61B 8/5215; G16H 50/50;
(Continued)

(56) References Cited

U.S. PATENT DOCUMENTS 10,430,946 B1   10/2019   Zhou et al.
10,631,828 B1 *  4/2020   Hare, II ............... A61B 8/0883
(Continued)

FOREIGN PATENT DOCUMENTS

WO   WO 2018026431 A1   2/2018
WO       2018/140596 A2   8/2018
(Continued)

OTHER PUBLICATIONS

U.S. Appl. No. 17/091,263, filed Nov. 6, 2020.
(Continued)

*Primary Examiner* — Mia M Thomas
(74) *Attorney, Agent, or Firm* — Seed IP Law Group LLP (57) ABSTRACT

A facility for processing a medical imaging image is described. The facility applies to the image a first machine learning model trained to recognize a view to which an image corresponds, and a second machine learning model trained to identify any of a set of anatomical features visualized in an image. The facility accesses a list of permitted anatomical features for images corresponding to the recognized view, and filters the identified anatomical features to exclude any not on the accessed list. The facility causes the accessed image to be displayed, overlaid with a visual indication of each of the filtered identified anatomical features.

25 Claims, 10 Drawing Sheets

(51) Int. Cl.
*G16H 50/20* (2018.01)
*G16H 50/50* (2018.01)
*A61B 8/14* (2006.01)
*A61B 8/08* (2006.01)
*G06T 7/00* (2017.01)
*G06K 9/62* (2022.01)
*G06T 11/00* (2006.01)
*G16H 30/20* (2018.01)
*G06N 3/04* (2006.01)
*G06N 3/08* (2006.01)

(52) U.S. Cl.
CPC .......... *A61B 8/5215* (2013.01); *G06K 9/6267* (2013.01); *G06N 3/0454* (2013.01); *G06N 3/08* (2013.01); *G06T 7/0012* (2013.01); *G06T 11/00* (2013.01); *G16H 30/20* (2018.01); *G16H 30/40* (2018.01); *G16H 50/20* (2018.01); *G16H 50/50* (2018.01); *G06T 2207/10132* (2013.01); *G06T 2207/20081* (2013.01); *G06T 2207/20084* (2013.01); *G06T 2207/30004* (2013.01); *G06T 2210/12* (2013.01)

(58) Field of Classification Search
CPC ........ G16H 30/20; G16H 50/20; G16H 30/40; G06K 9/6267; G06N 3/0454; G06N 3/08; G06T 7/0012; G06T 11/00
See application file for complete search history.

(56) References Cited

U.S. PATENT DOCUMENTS

| | | | |
|---|---|---|---|
| 2017/0360403 A1* | 12/2017 | Rothberg | A61B 8/5207 |
| 2018/0259608 A1* | 9/2018 | Golden | G06N 3/02 |
| 2019/0140596 A1 | 5/2019 | Shimamoto et al. | |
| 2019/0357869 A1* | 11/2019 | Madabhushi | A61B 5/4842 |
| 2020/0054306 A1* | 2/2020 | Mehanian | G06F 17/18 |
| 2020/0260062 A1* | 8/2020 | Sharma | H04N 13/122 |
| 2021/0321978 A1* | 10/2021 | Nguyen | A61B 8/5292 |
| 2021/0345986 A1* | 11/2021 | Cook | A61B 8/486 |
| 2021/0350529 A1* | 11/2021 | Ayinde | G06T 7/0012 |
| 2022/0061930 A1* | 3/2022 | Laviola | G06T 7/70 |
| 2022/0079528 A1* | 3/2022 | Cadieu | G06N 5/025 |
| 2022/0148158 A1* | 5/2022 | Ayinde | G06N 3/02 |
| 2022/0211348 A1* | 7/2022 | Zong | A61B 8/483 |

FOREIGN PATENT DOCUMENTS

| | | |
|---|---|---|
| WO | 2019/201726 A1 | 10/2019 |
| WO | WO 2020020809 A1 | 1/2020 |

OTHER PUBLICATIONS

U.S. Appl. No. 17/509,987, filed Oct. 25, 2021.
U.S. Appl. No. 17/529,565, filed Nov. 18, 2021.
U.S. Appl. No. 17/693,848, filed Mar. 14, 2022.
Liu, S. et al., "Deep learning in Medical Ultrasound Analysis: A Review," (2019). Engineering, 5(2): 261-275.
International Search Report and Written Opinion, dated Aug. 25, 2021, for International Application No. PCT/US2021/031415, 10 pages.
American Institute of Ultrasound in Medicine, "AIUM Practice Guideline for the Performance of the Focused Assessment With Sonography for Trauma (FAST) Examination," *J Ultrasound Med* 33:2047-2056, 2014.
Gal, Y., et al., "Dropout as a Bayesian Approximation: Representing Model Uncertainty in Deep Learning," Proceedings of the 33rd International Conference on Machine Learning, New York, NY, 2016, retrieved from arXiv:1506.02142v6, 12 pages.
Geifman, Y., et al., "Selective Classification for Deep Neural Networks," Jun. 2, 2017, retrieved from arXiv:1705.08500v2, 12 pages.
International Search Report and Written Opinion, dated Feb. 24, 2022, for International Application No. PCT/US2021/058037, (11 pages).
International Search Report and Written Opinion, dated Oct. 12, 2021, for International Application No. PCT/US2021/031193, 9 pages.
Lakshminarayanan, B., et al., "Simple and Scalable Predictive Uncertainty Estimation Using Deep Ensembles," 31st Conference on Neural Information Processing Systems (NIPS 2017), Long Beach, CA, retrieved from arXiv:1612.01474v3, 15 pages.
Redmon et al., "YOLOv3: An Incremental Improvement," Apr. 8, 2018, retrieved from arxiv.org/abs/1804.02767, 6 pages.

* cited by examiner

FIG. 7 allowed structure table 800

| view | allowed structure | |
|---|---|---|
| Apical 2 chambers | Left atrium | 801 |
| Apical 2 chambers | Left ventricle | 802 |
| Apical 2 chambers | Mitral valve | 803 |
| Apical 3 chambers (Apical long axis) | Aorta | 804 |
| Apical 3 chambers (Apical long axis) | Left atrium | 805 |
| Apical 3 chambers (Apical long axis) | Left ventricle | 806 |
| Apical 3 chambers (Apical long axis) | Left ventricular outflow tract | 807 |
| Apical 3 chambers (Apical long axis) | Mitral valve | 808 |
| Apical 4 chambers | Aorta | 809 |
| Apical 4 chambers | Interatrial septum | 810 |
| Apical 4 chambers | Interventricular septum | 811 |
| Apical 4 chambers | Left atrium | 812 |
| Apical 4 chambers | Left ventricle | 813 |
| Apical 4 chambers | Left ventricular outflow tract | 814 |
| Apical 4 chambers | Mitral valve | 815 |
| Apical 4 chambers | Right atrium | 816 |
| Apical 4 chambers | Right ventricle | 817 |
| Apical 4 chambers | Tricuspid valve | 818 |
| Apical 5 chambers | Aorta | 819 |
| Apical 5 chambers | Interatrial septum | 820 |
| Apical 5 chambers | Interventricular septum | 821 |
| Apical 5 chambers | Left atrium | 822 |
| Apical 5 chambers | Left ventricle | 823 |
| Apical 5 chambers | Left ventricular outflow tract | 824 |
| Apical 5 chambers | Mitral valve | 825 |
| Apical 5 chambers | Right atrium | 826 |
| Apical 5 chambers | Right ventricle | 827 |
| Apical 5 chambers | Tricuspid valve | 828 |
| ... | ... | |

851 = view column; 852 = allowed structure column

AUTOMATICALLY IDENTIFYING ANATOMICAL STRUCTURES IN MEDICAL IMAGES IN A MANNER THAT IS SENSITIVE TO THE PARTICULAR VIEW IN WHICH EACH IMAGE IS CAPTURED

CROSS-REFERENCE TO RELATED APPLICATIONS

This Application claims the benefit of U.S. Provisional Patent Application No. 63/022,986, filed May 11, 2020 and entitled "CLASSIFYING OUT-OF-DISTRIBUTION RESULTS FROM OBJECT DETECTION OR SEGMENTATION OF ULTRASOUND IMAGES," which is hereby incorporated by reference in its entirety.

In cases where the present application conflicts with a document incorporated by reference, the present application controls.

BACKGROUND

Ultrasound imaging is a useful medical imaging modality. For example, internal structures of a patient's body may be imaged before, during or after a therapeutic intervention. A healthcare professional typically holds a portable ultrasound probe, sometimes called a "transducer," in proximity to the patient and moves the transducer as appropriate to visualize one or more target structures in a region of interest in the patient. A transducer may be placed on the surface of the body or, in some procedures, a transducer is inserted inside the patient's body. The healthcare professional coordinates the movement of the transducer so as to obtain a desired representation on a screen, such as a two-dimensional cross-section of a three-dimensional volume.

Particular views of an organ or other tissue or body feature (such as fluids, bones, joints or the like) can be clinically significant. Such views may be prescribed by clinical standards as views that should be captured by the ultrasound operator, depending on the target organ, diagnostic purpose or the like.

In some ultrasound images, it is useful to identify anatomical structures visualized in the image. For example in an ultrasound image view showing a particular organ, it can be useful to identify constituent structures within the organ. As one example, in some views of the heart, constituent structures are visible, such as the left and right atria; left and right ventricles; and aortic, mitral, pulmonary, and tricuspid valves.

Existing software solutions have sought to identify such structures automatically. These existing solutions seek to "detect" structures by specifying a bounding box in which each is visible, or "segment" structures by tracing each structure's boundaries in the image.

DETAILED DESCRIPTION

The inventors have recognized that conventional approaches to automatically identifying constituent structures of organs shown in ultrasound images have significant disadvantages. In particular, these conventional approaches frequently produce false positives; that is, they identify structures that aren't actually present in the image. This is particularly common in cases where an organ contains multiple structures of similar size and shape, such as the four valves of the heart. In some cases, conventional approaches seek to reduce or eliminate the problem of false positives by significantly elevating a confidence threshold operating parameter that limits the structures identified to those having confidence values higher than the threshold. In order to eliminate most or all false positives, this confidence threshold must be set so high that it creates the opposite problem: false negatives, in which structures that are actually visible are omitted from the identification results.

In response to recognizing these disadvantages, the inventors have conceived and reduced to practice a software and/or hardware facility that automatically identifies anatomical structures in medical images such as ultrasound and images in a manner that is sensitive to the particular view in which each image is captured ("the facility"). By doing so, the facility can set the confidence threshold operating parameter relatively low, so as to minimize the occurrence of false negatives. At the same time, the facility minimizes the occurrence of false positives by limiting the identified structures to those that are typically visible in the view in which an image is captured. In some embodiments, the facility automatically determines the view in which each image is captured using image recognition machine learning techniques.

In one example of the operation of the facility discussed further below, the facility uses image recognition machine learning techniques to identify five candidate structures in an image of a human heart. The facility uses image recognition machine learning techniques to classify this image as being from an "Apical four chambers" view of the heart. Based on this classification, the facility accesses a list of structures that are allowed to be identified in images of the heart captured from this view. By comparing this list of allowed structures to the five identified candidate structures, the facility determines that only four of the identified candidate structures occur in the list. In response, the facility identifies among the five identified candidate structures only the four that occur in the list.

By operating in some or all of the ways described above, the facility automatically identifies anatomical structures in medical images with greater accuracy than is conventionally possible.

Additionally, the facility improves the functioning of computer or other hardware, such as by reducing the dynamic display area, processing, storage, and/or data transmission resources needed to perform a certain task, thereby enabling the task to be permitted by less capable, capacious, and/or expensive hardware devices, and/or be performed with lesser latency, and/or preserving more of the conserved resources for use in performing other tasks. For example, by maximizing the usability of an initial medical image by more frequently identifying all structures visualized therein with significantly fewer false positives, the facility avoids many cases in which re-imaging is required. By reducing the need to reimage, the facility consumes, overall, less memory and processing resources to capture additional images and perform additional rounds of automatic structure identification.

Figure 1:
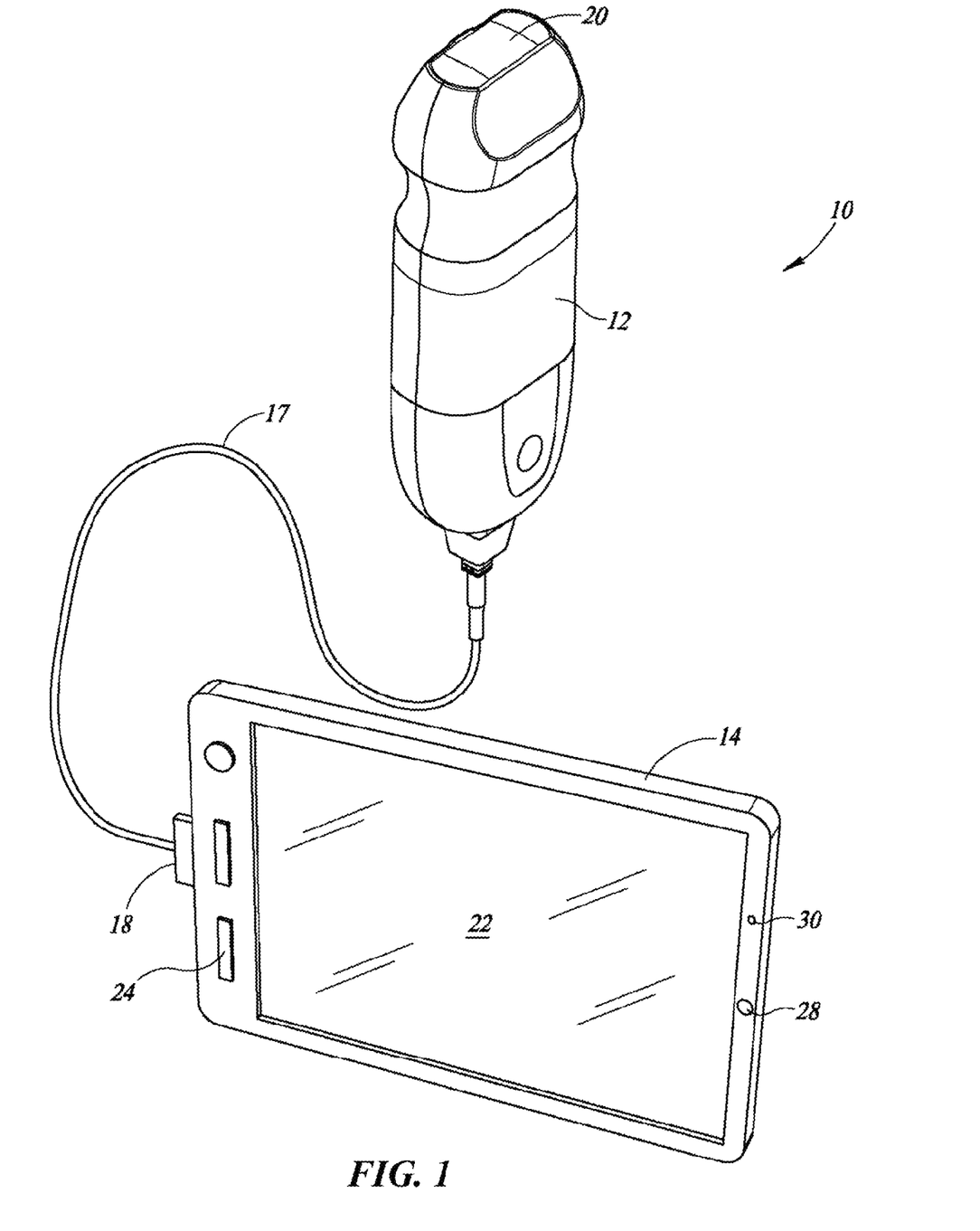
FIG. 1 is a schematic illustration of a physiological sensing device 10, in accordance with one or more embodiments of the present disclosure.

FIG. 1 is a schematic illustration of a physiological sensing device 10, in accordance with one or more embodiments of the present disclosure. The device 10 includes a probe 12 that, in the illustrated embodiment, is electrically coupled to a handheld computing device 14 by a cable 17. The cable 17 includes a connector 18 that detachably connects the probe 12 to the computing device 14. The handheld computing device 14 may be any portable computing device having a display, such as a tablet computer, a smartphone, or the like. In some embodiments, the probe 12 need not be electrically coupled to the handheld computing device 14, but may operate independently of the handheld computing device 14, and the probe 12 may communicate with the handheld computing device 14 via a wireless communication channel.

The probe 12 is configured to transmit an ultrasound signal toward a target structure and to receive echo signals returning from the target structure in response to transmission of the ultrasound signal. The probe 12 includes an ultrasound sensor 20 that, in various embodiments, may include an array of transducer elements (e.g., a transducer array) capable of transmitting an ultrasound signal and receiving subsequent echo signals.

The device 10 further includes processing circuitry and driving circuitry. In part, the processing circuitry controls the transmission of the ultrasound signal from the ultrasound sensor 20. The driving circuitry is operatively coupled to the ultrasound sensor 20 for driving the transmission of the ultrasound signal, e.g., in response to a control signal received from the processing circuitry. The driving circuitry and processor circuitry may be included in one or both of the probe 12 and the handheld computing device 14. The device 10 also includes a power supply that provides power to the driving circuitry for transmission of the ultrasound signal, for example, in a pulsed wave or a continuous wave mode of operation.

The ultrasound sensor 20 of the probe 12 may include one or more transmit transducer elements that transmit the ultrasound signal and one or more receive transducer elements that receive echo signals returning from a target structure in response to transmission of the ultrasound signal. In some embodiments, some or all of the transducer elements of the ultrasound sensor 20 may act as transmit transducer elements during a first period of time and as receive transducer elements during a second period of time that is different than the first period of time (i.e., the same transducer elements may be usable to transmit the ultrasound signal and to receive echo signals at different times).

The computing device 14 shown in FIG. 1 includes a display screen 22 and a user interface 24. The display screen 22 may be a display incorporating any type of display technology including, but not limited to, LCD or LED display technology. The display screen 22 is used to display one or more images generated from echo data obtained from the echo signals received in response to transmission of an ultrasound signal, and in some embodiments, the display screen 22 may be used to display color flow image information, for example, as may be provided in a Color Doppler imaging (CDI) mode. Moreover, in some embodiments, the display screen 22 may be used to display audio waveforms, such as waveforms representative of an acquired or conditioned auscultation signal.

In some embodiments, the display screen 22 may be a touch screen capable of receiving input from a user that touches the screen. In such embodiments, the user interface 24 may include a portion or the entire display screen 22, which is capable of receiving user input via touch. In some embodiments, the user interface 24 may include one or more buttons, knobs, switches, and the like, capable of receiving input from a user of the ultrasound device 10. In some embodiments, the user interface 24 may include a microphone 30 capable of receiving audible input, such as voice commands.

The computing device 14 may further include one or more audio speakers 28 that may be used to output acquired or conditioned auscultation signals, or audible representations of echo signals, blood flow during Doppler ultrasound imaging, or other features derived from operation of the device 10.

The probe 12 includes a housing, which forms an external portion of the probe 12. The housing includes a sensor portion located near a distal end of the housing, and a handle portion located between a proximal end and the distal end of the housing. The handle portion is proximally located with respect to the sensor portion.

The handle portion is a portion of the housing that is gripped by a user to hold, control, and manipulate the probe 12 during use. The handle portion may include gripping features, such as one or more detents, and in some embodiments, the handle portion may have a same general shape as portions of the housing that are distal to, or proximal to, the handle portion.

The housing surrounds internal electronic components and/or circuitry of the probe 12, including, for example, electronics such as driving circuitry, processing circuitry, oscillators, beamforming circuitry, filtering circuitry, and the like. The housing may be formed to surround or at least partially surround externally located portions of the probe 12, such as a sensing surface. The housing may be a sealed housing, such that moisture, liquid or other fluids are prevented from entering the housing. The housing may be formed of any suitable materials, and in some embodiments, the housing is formed of a plastic material. The housing may be formed of a single piece (e.g., a single material that is molded surrounding the internal components) or may be formed of two or more pieces (e.g., upper and lower halves) which are bonded or otherwise attached to one another.

In some embodiments, the probe 12 includes a motion sensor. The motion sensor is operable to sense a motion of the probe 12. The motion sensor is included in or on the probe 12 and may include, for example, one or more accelerometers, magnetometers, or gyroscopes for sensing motion of the probe 12. For example, the motion sensor may be or include any of a piezoelectric, piezoresistive, or capacitive accelerometer capable of sensing motion of the probe 12. In some embodiments, the motion sensor is a tri-axial motion sensor capable of sensing motion about any of three axes. In some embodiments, more than one motion sensor 16 is included in or on the probe 12. In some embodiments, the motion sensor includes at least one accelerometer and at least one gyroscope.

The motion sensor may be housed at least partially within the housing of the probe 12. In some embodiments, the motion sensor is positioned at or near the sensing surface of the probe 12. In some embodiments, the sensing surface is a surface which is operably brought into contact with a patient during an examination, such as for ultrasound imaging or auscultation sensing. The ultrasound sensor 20 and one or more auscultation sensors are positioned on, at, or near the sensing surface.

In some embodiments, the transducer array of the ultrasound sensor 20 is a one-dimensional (1D) array or a two-dimensional (2D) array of transducer elements. The transducer array may include piezoelectric ceramics, such as lead zirconate titanate (PZT), or may be based on microelectromechanical systems (MEMS). For example, in various embodiments, the ultrasound sensor 20 may include piezoelectric micromachined ultrasonic transducers (PMUT), which are microelectromechanical systems (MEMS)-based piezoelectric ultrasonic transducers, or the ultrasound sensor 20 may include capacitive micromachined ultrasound transducers (CMUT) in which the energy transduction is provided due to a change in capacitance.

The ultrasound sensor 20 may further include an ultrasound focusing lens, which may be positioned over the transducer array, and which may form a part of the sensing surface. The focusing lens may be any lens operable to focus a transmitted ultrasound beam from the transducer array toward a patient and/or to focus a reflected ultrasound beam from the patient to the transducer array. The ultrasound focusing lens may have a curved surface shape in some embodiments. The ultrasound focusing lens may have different shapes, depending on a desired application, e.g., a desired operating frequency, or the like. The ultrasound focusing lens may be formed of any suitable material, and in some embodiments, the ultrasound focusing lens is formed of a room-temperature-vulcanizing (RTV) rubber material.

In some embodiments, first and second membranes are positioned adjacent to opposite sides of the ultrasound sensor 20 and form a part of the sensing surface. The membranes may be formed of any suitable material, and in some embodiments, the membranes are formed of a room-temperature-vulcanizing (RTV) rubber material. In some embodiments, the membranes are formed of a same material as the ultrasound focusing lens.

Figure 2:
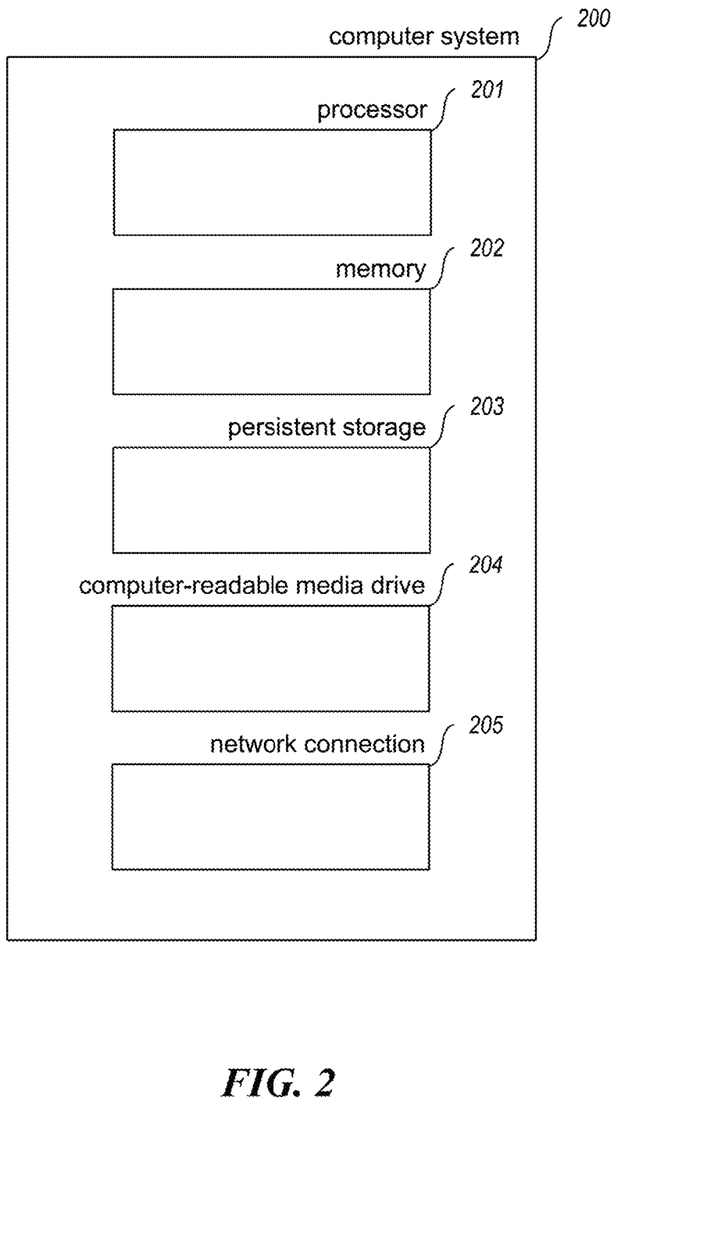
FIG. 2 is a block diagram showing some of the components typically incorporated in at least some of the computer systems and other devices on which the facility operates.

FIG. 2 is a block diagram showing some of the components typically incorporated in at least some of the computer systems and other devices on which the facility operates. In various embodiments, these computer systems and other devices 200 can include server computer systems, cloud computing platforms or virtual machines in other configurations, desktop computer systems, laptop computer systems, netbooks, mobile phones, personal digital assistants, televisions, cameras, automobile computers, electronic media players, physiological sensing devices, and/or their associated display devices, etc. In various embodiments, the computer systems and devices include zero or more of each of the following: a processor 201 for executing computer programs and/or training or applying machine learning models, such as a CPU, GPU, TPU, NNP, FPGA, or ASIC; a computer memory 202 for storing programs and data while they are being used, including the facility and associated data, an operating system including a kernel, and device drivers; a persistent storage device 203, such as a hard drive or flash drive for persistently storing programs and data; a computer-readable media drive 204, such as a floppy, CD-ROM, or DVD drive, for reading programs and data stored on a computer-readable medium; and a network connection 205 for connecting the computer system to other computer systems to send and/or receive data, such as via the Internet or another network and its networking hardware, such as switches, routers, repeaters, electrical cables and optical fibers, light emitters and receivers, radio transmitters and receivers, and the like. While computer systems configured as described above are typically used to support the operation of the facility, those skilled in the art will appreciate that the facility may be implemented using devices of various types and configurations, and having various components.

Figure 3:
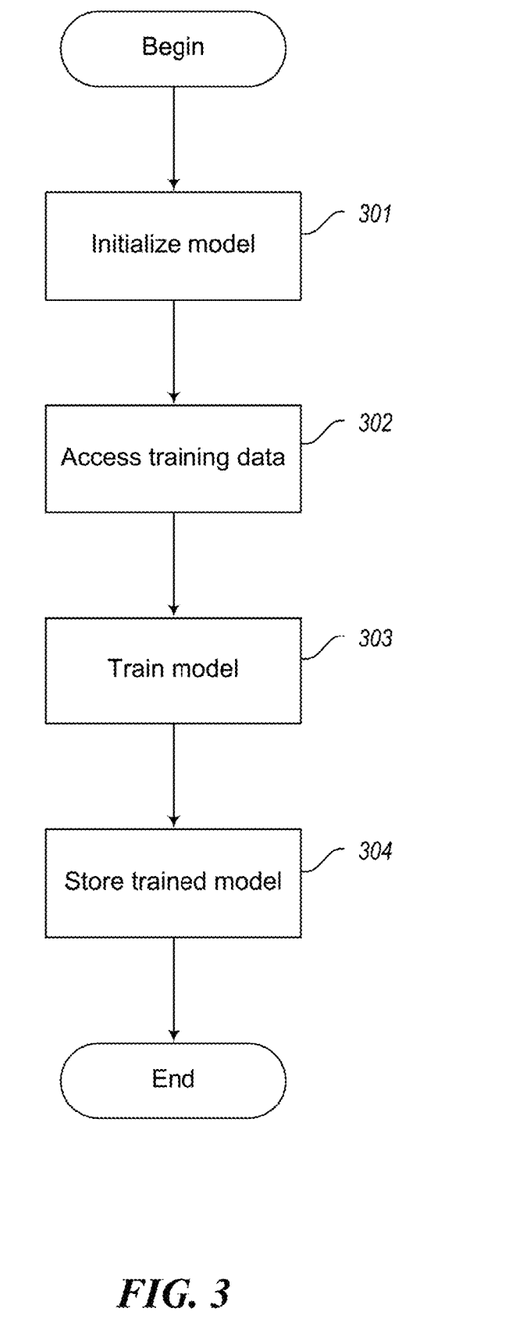
FIG. 3 is a flow diagram showing a process performed by the facility in some embodiments to train one or more machine learning models to predict view for and detect structures in a medical image.

FIG. 3 is a flow diagram showing a process performed by the facility in some embodiments to train one or more machine learning models to predict view for and detect structures in a medical image. In some embodiments, this process executes on a server. In act 301, the facility initializes the model.

Figure 4:
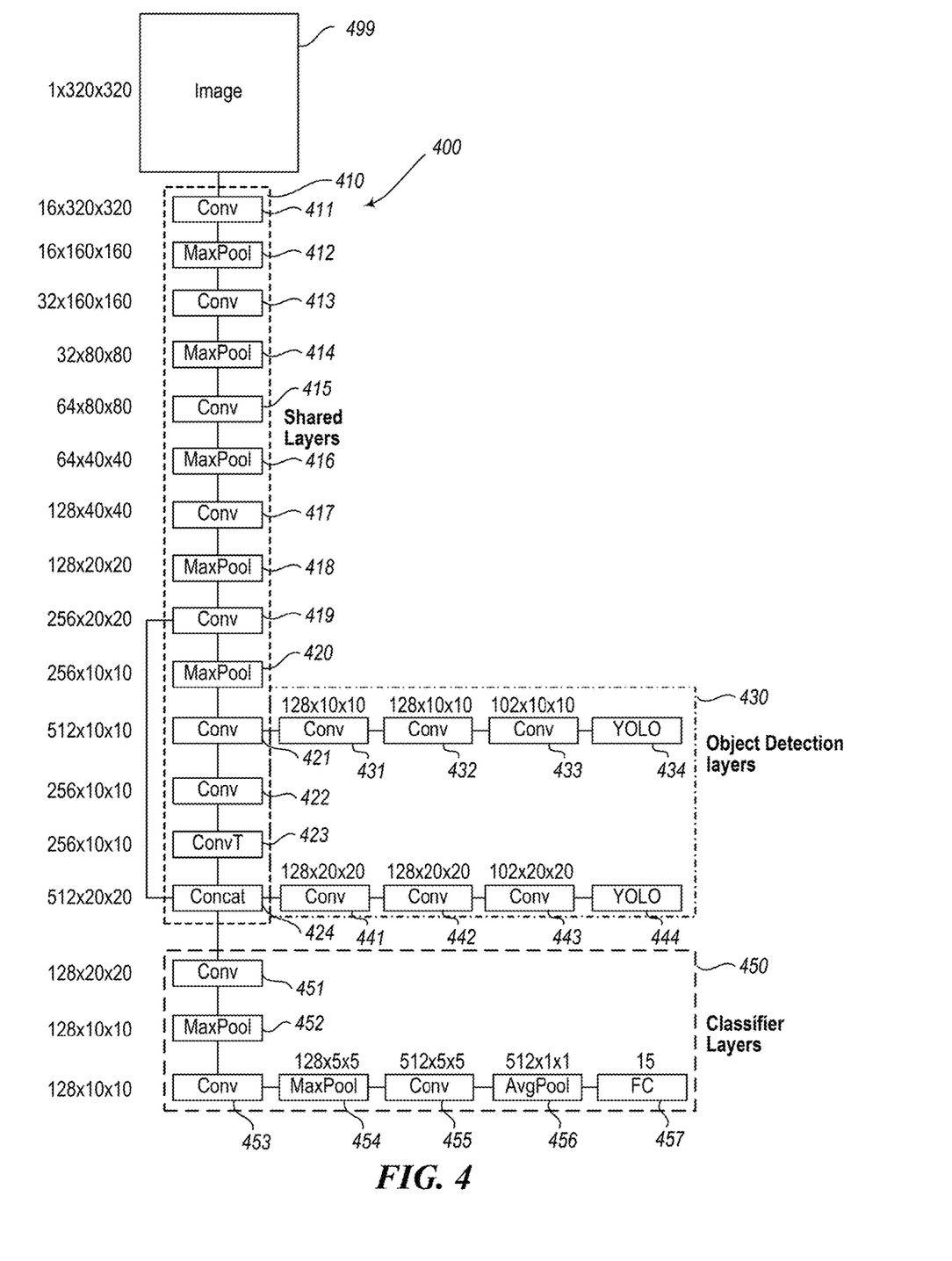
FIG. 4 is a model diagram showing a model architecture used by the facility in some embodiments.

FIG. 4 is a model diagram showing a model architecture used by the facility in some embodiments. The model architecture 400 includes shared layers 410 used by the facility both for structure detection and view classification; object detection layers 430 used by the facility only to perform structure detection; and classifier layers 450 used by the facility only to perform view classification. For each of the layers, FIG. 4 shows a layer type and layer size. Layer type is expressed in terms of the following abbreviations:

TABLE 1

| Abbreviation | Layer Type |
| --- | --- |
| AvgPool | Average Pooling layer |
| Concat | Concatenation layer |
| Conv | Convolutional layer |
| ConvT | Transposed Convolutional layer |
| FC | Fully-Connected layer |
| MaxPool | Maximum Pooling layer |
| YOLO | You Only Look Once layer |

For example, layer 411, shown with the type abbreviation "Cony," is a Convolutional layer. Layer size is expressed with the dimensions number of output values per pixel× number of pixels in horizontal dimension×number of pixels in vertical dimension. For example, layer 411, shown with the dimensions 16×320×320, outputs 16 values per pixel, in a rectangular array of 320 pixels by 320 pixels.

Returning to FIG. 3, in act 302, the facility accesses training data. In some embodiments, the training data is obtained as follows: 3-5 second long ultrasound video clips are captured and annotated by expert sonographers or cardiologists. A manually-curated test set of 100 or more video clips evenly distributed across all possible views are set aside for final evaluation. Of the remaining data, 10% is held out as a validation set during training. The validation set is equally stratified by device type and view. The remaining data is used for training. For model preprocessing, input images are resized to 320×320 pixels, and pixel values are scaled between 0.0 and 1.0. For the training data only, input images are also randomly augmented to increase diversity in training input. Augmentation transformations include, in various embodiments: flipping horizontally or vertically, rotation, scaling (zoom in/out), translation, blurring, contrast/brightness scaling, and random pixel dropout, among others.

In act 303, the facility uses the accessed training data to train the model. In some embodiments, model training is a two-step process. First, the model is trained only for the object detection task, and the classifier layers are not used. Then, the model is trained for the classification task, and the network weight parameters for the shared layers are frozen, and the object detection layers are not used. In some embodiments, for each step, the facility trains the network with a batch size of 512 for 1000 epochs using Adam optimizer, with an exponentially decaying learning rate starting at 0.001 and ending at 0.0001.

In act 304, the facility stores the trained model. In some embodiments, act 304 involves saving neural network connection weights determined during training. In some embodiments, act 304 includes distributing the trained model to devices on which it will be used to evaluate production images, such as each of a number of portable imaging devices. After act 304, this process concludes. In some embodiments, this process can be repeated for a variety of purposes, including improving model accuracy; adding new views, structures, imaging modalities, or device designs; etc.

Those skilled in the art will appreciate that the acts shown in FIG. 3 and any flow diagrams discussed below may be altered in a variety of ways. For example, the order of the acts may be rearranged; some acts may be performed in parallel; shown acts may be omitted, or other acts may be included; a shown act may be divided into sub-acts, or multiple shown acts may be combined into a single act, etc.

Figure 5:
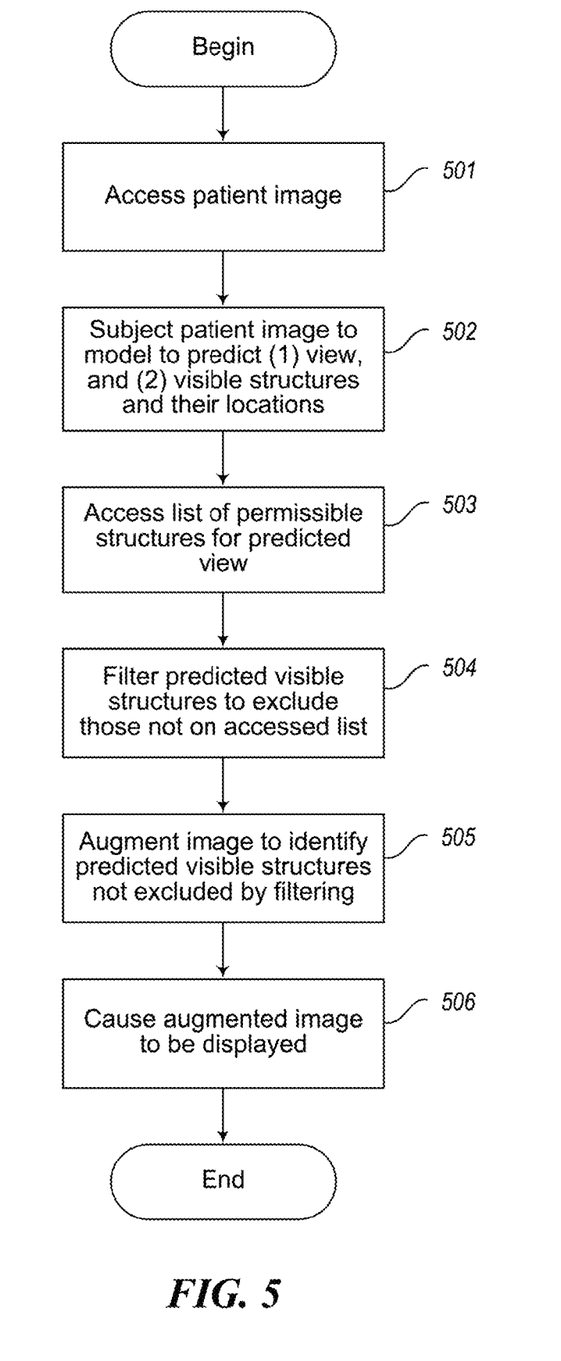
FIG. 5 is a flow diagram showing a process performed by the facility in some embodiments to process a patient image in production.

FIG. 5 is a flow diagram showing a process performed by the facility in some embodiments to process a patient image in production. In some embodiments, the facility performs this process on each of one or more portable imaging devices. In some embodiments, the facility performs this process with respect to each patient image captured by one of these portable imaging devices. In some embodiments, the facility performs this process on one or more physical servers, and/or one or more virtual servers, such as virtual cloud servers. In act 501, the facility accesses a patient image. In some embodiments, the patient image is an ultrasound image that has been contemporaneously captured by an ultrasound sensor.

Figure 6:
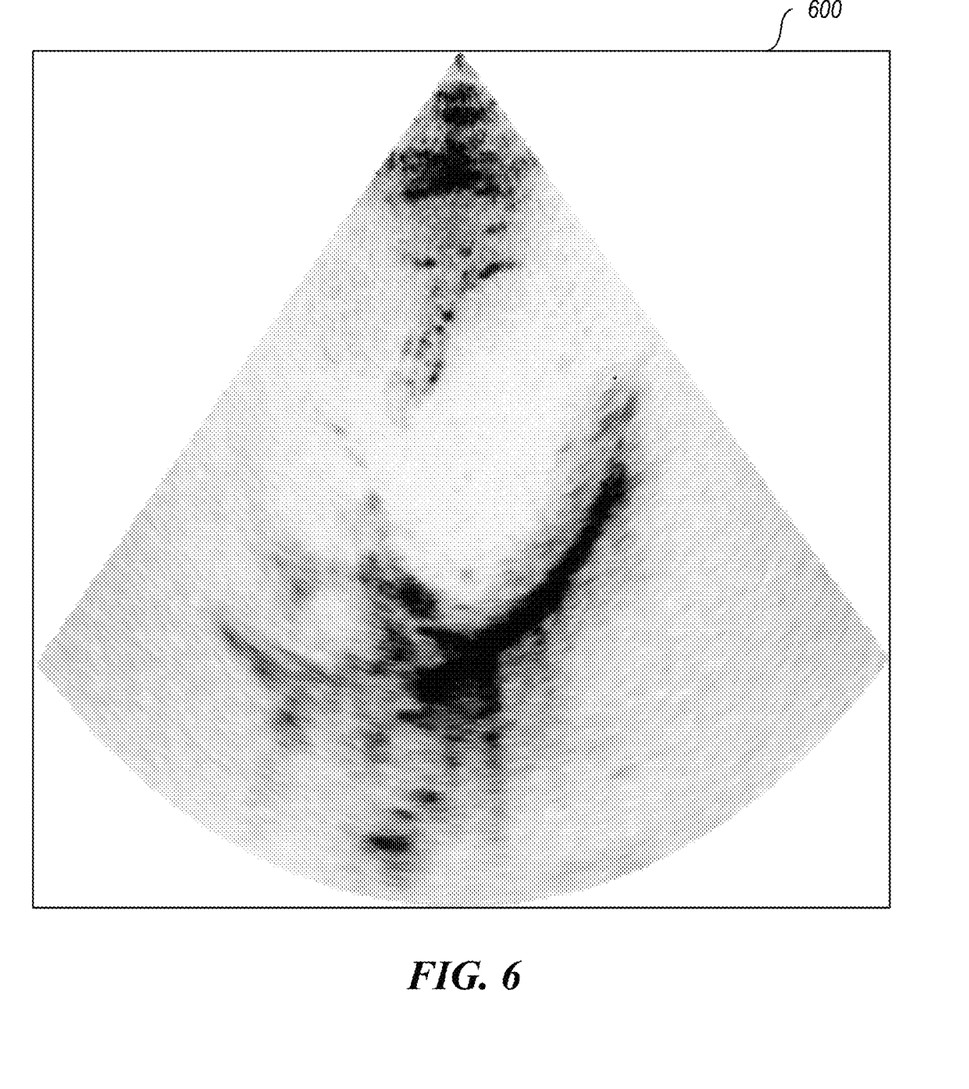
FIG. 6 is a medical imaging diagram showing a sample patient image accessed by the facility.

FIG. 6 is a medical imaging diagram showing a sample patient image accessed by the facility. The patient image 600 is an ultrasound image. This ultrasound image, also shown in FIGS. 7 and 9 discussed below, has been grayscale-inverted in order to be more easily and faithfully produced in patent drawings.

Returning to FIG. 5, in act 502, the facility subjects the patient image accessed in act 501 to one or more trained machine learning models in order to predict both the view represented by the patient image, and which structures are visualizable (i.e., visible) and their locations.

Figure 7:
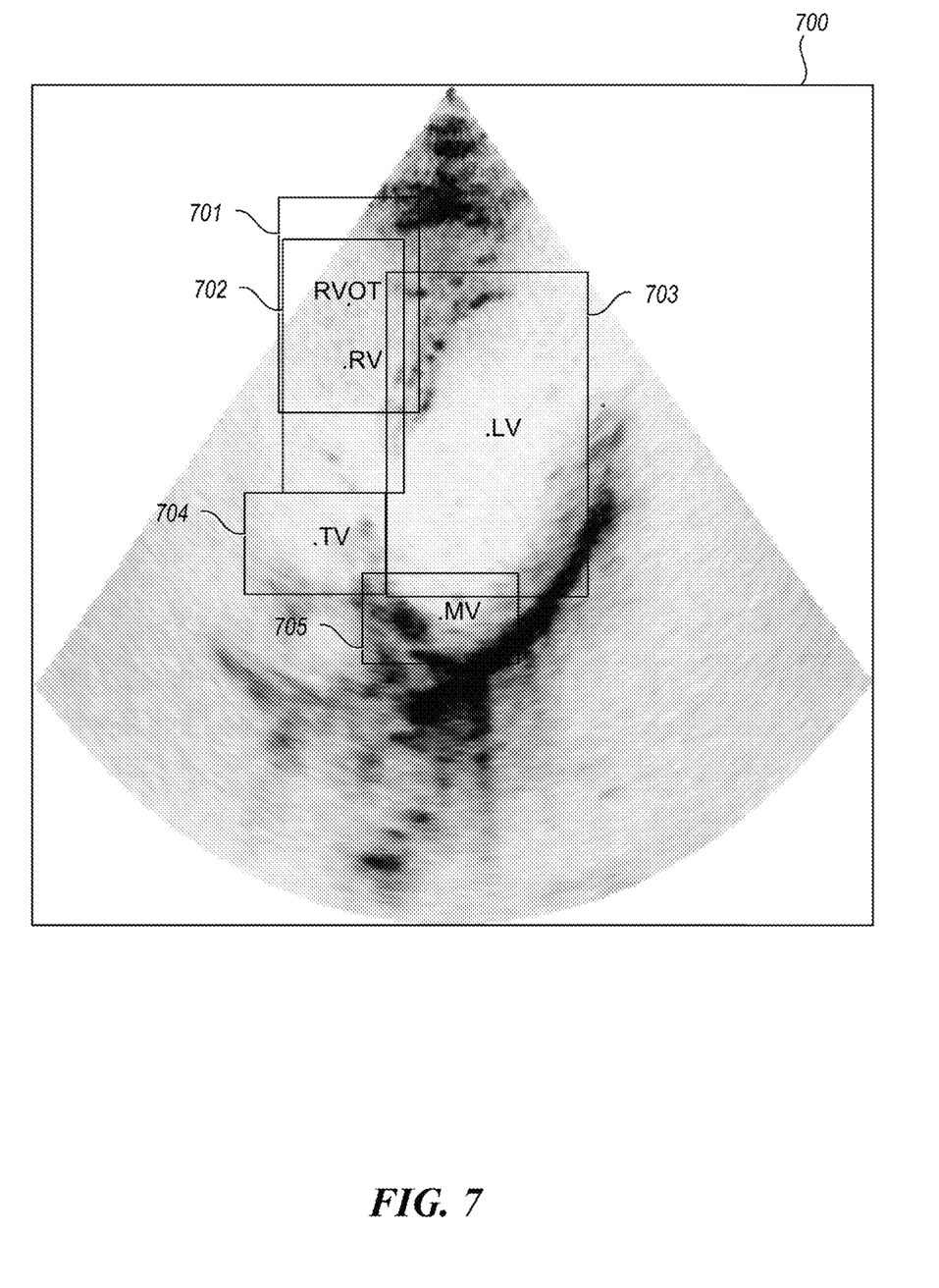
FIG. 7 is a medical imaging diagram showing the sample patient image, annotated to show the structures identified in it by the facility.

FIG. 7 is a medical imaging diagram showing the sample patient image, annotated to show the structures identified in it by the facility. In particular, patient image 700 is annotated to show the following structures, each shown with a dot in the middle and a bounding rectangle: right ventricular outflow tract 701, right ventricle 702, left ventricle 703, tricuspid valve 704, and mitral valve 705. In processing the sample patient image, the facility also determines that it represents an apical four chambers view (not shown).

Returning to FIG. 5, in act 503, the facility accesses a list of permissible structures for the view predicted in act 502.

Figure 8:
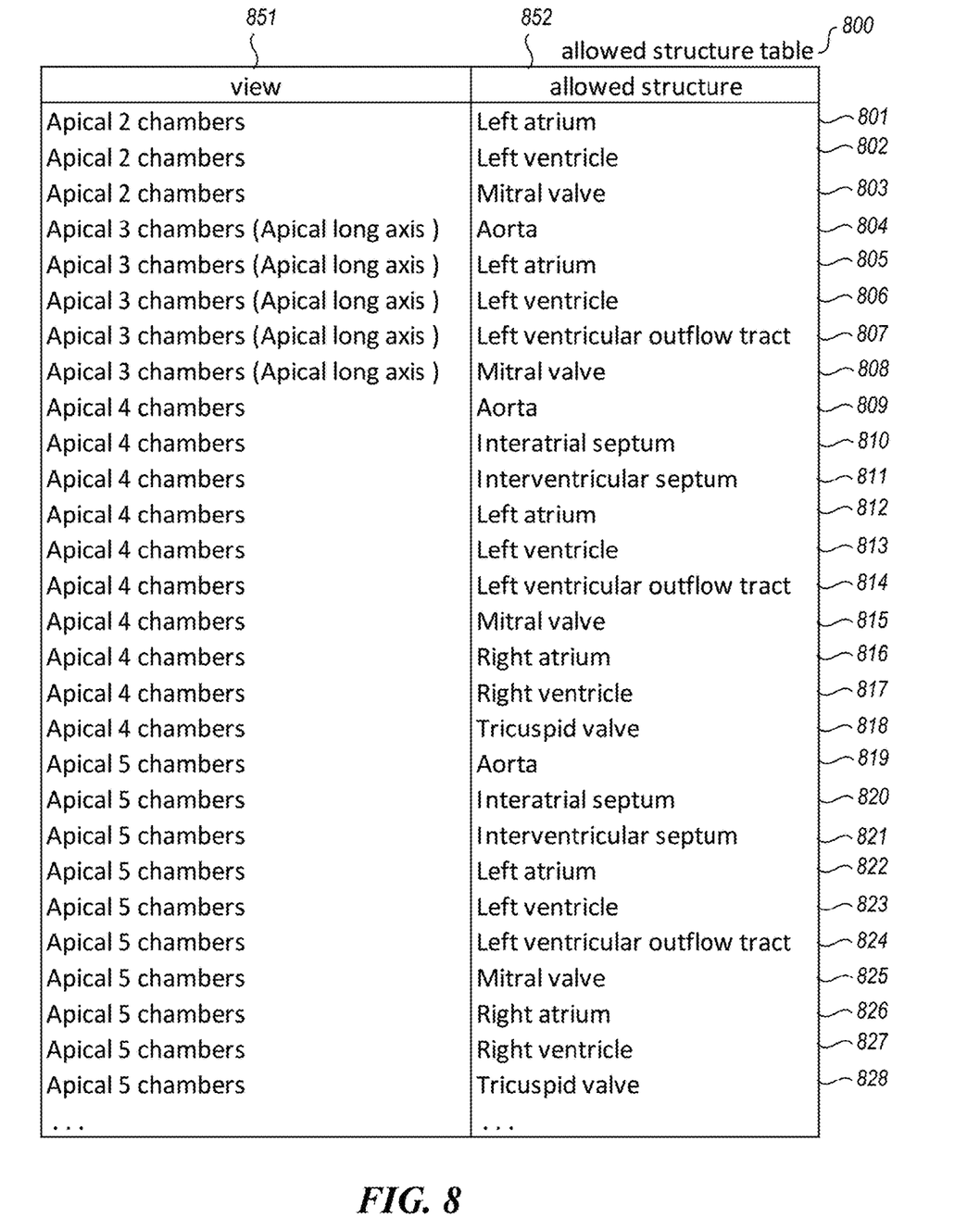
FIG. 8 is a table diagram showing sample contents of a table used by the facility in some embodiments to store lists of permitted structures for different views.

FIG. 8 is a table diagram showing sample contents of an allowed structure table used by the facility in some embodiments to store lists of permitted structures for different views. The allowed structure table 800 is made up of rows, such as rows 801-828, each corresponding to a different combination of a view and a structure allowed in that view. Each row is divided into a view column 851 identifying the view, and an allowed structure column 852 identifying and labeling structure for the view. For example, row 808 indicates that, in an apical four chambers view, the mitral valve is an allowed structure. In various embodiments, the lists shown in the allowed structure table are manually generated as a matter of editorial discretion; compiled automatically from the labels on the training images; etc.

In order to access a list of permissible structures for a particular view, the facility selects the rows of the allowed structure table in which that view occurs in the view column, and extracts from the selected rows the structures that occur in the allowed structure column. In the context of the example, in which the predicted view is the apical four chambers view, the facility selects rows 809-818, to obtain the following ten permitted structures: Aorta, Interatrial septum, Interventricular septum, Left atrium, Left ventricle, Left ventricular outflow tract, Mitral valve, Right atrium, Right ventricle, and Tricuspid valve.

While FIG. 8 shows a table whose contents and organization are designed to make them more comprehensible by a human reader, those skilled in the art will appreciate that actual data structures used by the facility to store this information may differ from the table shown, in that they, for example, may be organized in a different manner; may contain more or less information than shown; may be encoded, compressed, encrypted, and/or indexed; may contain a much larger number of rows than shown, etc.

Returning to FIG. 5, in act 504, the facility filters the visible structures predicted in act 502 to exclude those not on the list of permitted structures accessed in act 503. In the context of the example, the facility matches the following predicted structures to the list accessed in act 503 for the apical four chambers view: right ventricle, left ventricle, tricuspid valve, and mitral valve. Failing to match the right ventricular outflow tract, the facility excludes this structure, such that only the four structures listed above remain. In act 505, the facility augments the patient image accessed in act 501 to identify all of the visible structures predicted in act 502 that were not excluded by the filtering of act 504.

Figure 9:
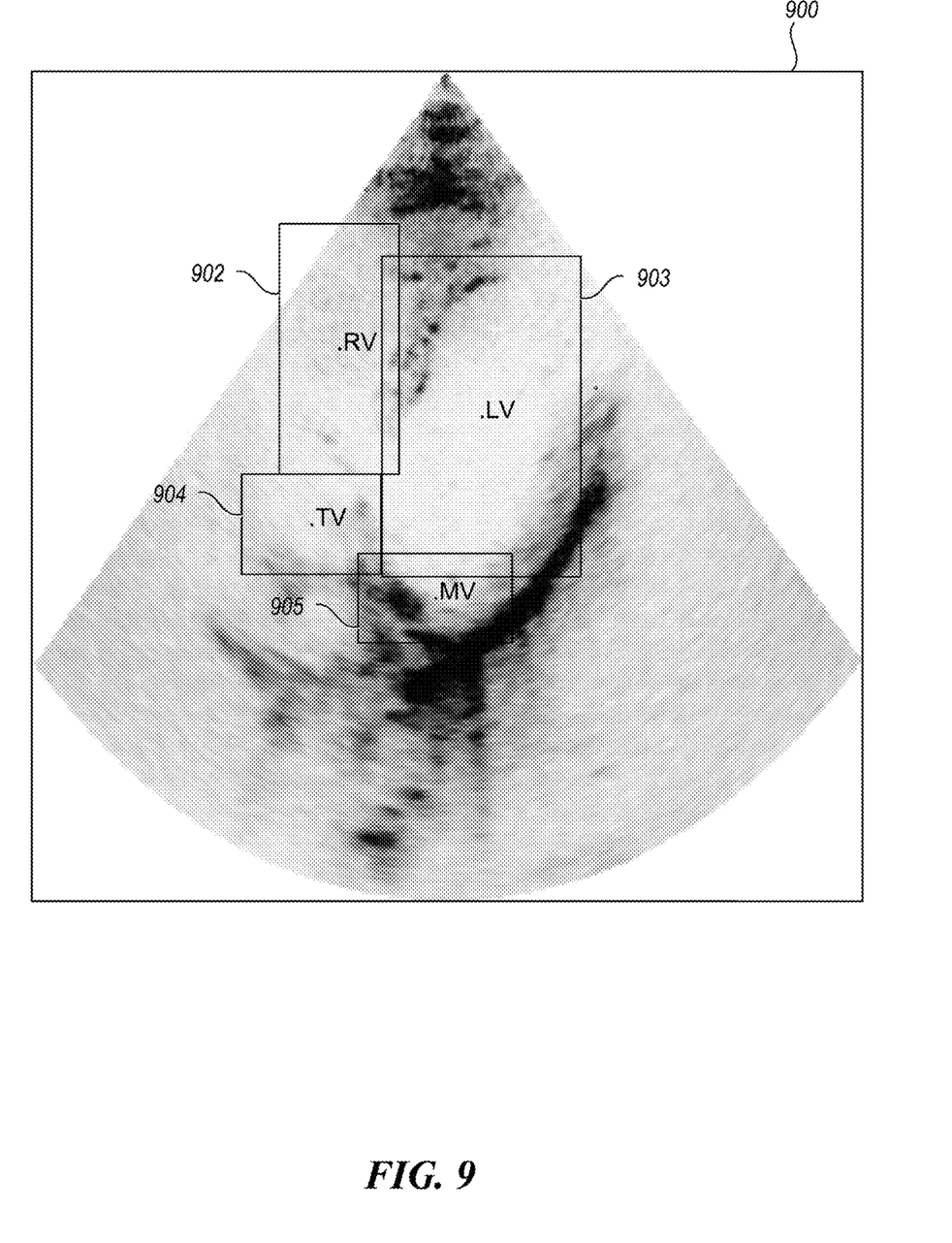
FIG. 9 is a medical imaging diagram showing the sample patient image, annotated to show the structures identified in it by the facility, filtered to those structures permitted for the predicted view.

FIG. 9 is a medical imaging diagram showing the sample patient image, annotated to show the structures identified in it by the facility, filtered to those structures permitted for the predicted view. By comparing FIG. 9 to FIG. 6, it can be seen that the facility has added annotations for the right ventricle 902, left ventricle 903, tricuspid valve 904, and mitral valve 905. In each case, the annotation shown includes a full name or abbreviation for the structure, a dot in the structure's center, and a bounding rectangle. These annotations omit the left ventricular outflow tract 701 shown in FIG. 7, which is not permitted for the apical four chambers view. In some embodiments (not shown), the facility traces the border of each identified structure as part of annotating the patient image.

Returning to FIG. 5, in act 506, the facility causes the augmented image created in act 505 to be displayed, such as on a display device integrated into or connected to the medical imaging device that generated the patient image. In some embodiments (not shown), the facility also persistently stores the augmented image and/or transmits it elsewhere for storage, review, and/or analysis. After act 506, this process concludes.

Figure 10:
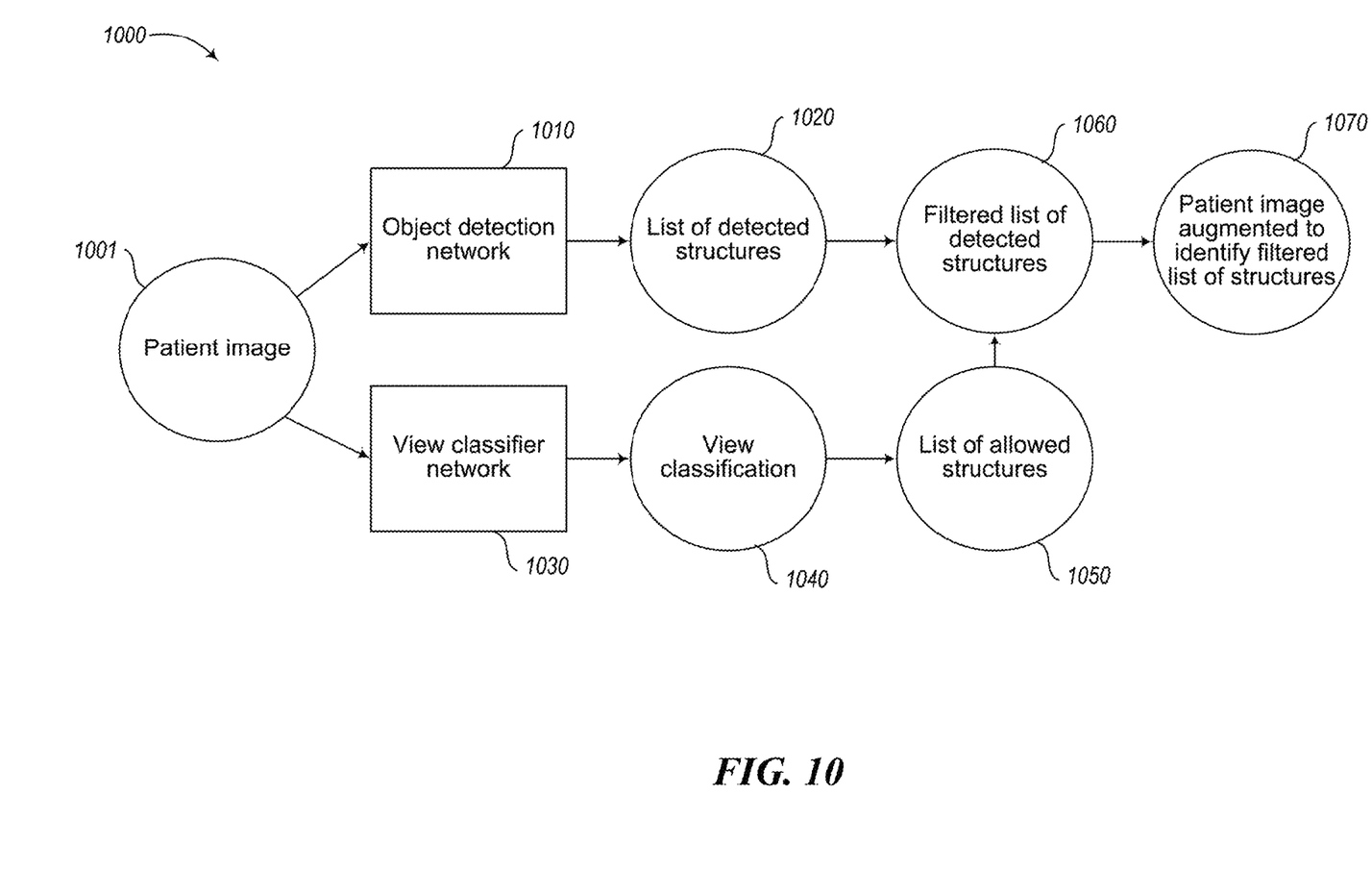
FIG. 10 is a data flow diagram illustrating data flows that occur in the facility in some embodiments.

FIG. 10 is a data flow diagram illustrating data flows that occur in the facility in some embodiments. In the data flow 1000, a patient image 1001 is subjected to both and object detection network 1010 and a view classifier network 1030. As discussed above, in various embodiments, these networks are independent, intersecting, or indistinguishably merged. The object detection network generates a list 1020 of structures detected in the patient image. The view classifier network generates a view classification 1040 for the patient image. From this view classification, the facility generates a list 1050 of allowed structures. The facility uses the list of allowed structures to filter the list of detected structures and obtain a filtered list 1060 of detected structures. The facility uses the filtered list of detected structures to generate a copy 1070 of the patient image that is augmented to identify the filtered list of structures.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A system, comprising:
an ultrasound sensing device; and
a computing device, the computing device comprising:
  a communication interface configured to directly receive ultrasound echo data sensed by the ultrasound sensing device from a person, the received ultrasound echo data comprising an ultrasound image;
  a memory configured to:
    store one or more first neural networks trained to identify physiological structures in ultrasound images,
    store one or more second neural networks trained to classify an ultrasound image as having been captured in a particular view, and
    store, for each of a set of ultrasound views, a list of permitted anatomical structures to identify in the ultrasound view;
  a processor configured to:
    apply to the received ultrasound image the one or more trained first neural networks to identify a set of physiological structures in the received ultrasound image,
    apply to the received ultrasound image the one or more trained second neural networks to classify the received ultrasound image as having been captured in a particular view,
    access the list of permitted anatomical structures for the classified view, and
    select in the set of physiological structures identified in the received ultrasound image only those that occur in the accessed list;
  a display device configured to:
    display the received ultrasound image; and
    display together with the ultrasound image annotations visually indicating the selected physiological structures of the set.

2. The system of claim 1 wherein the ultrasound sensing device comprises a transducer.

3. The system of claim 1 wherein each of the set of ultrasound views is a view featuring a particular organ, and the permitted anatomical structures listed for each of the set of ultrasound views are constituent structures of that organ.

4. One or more instances of non-transitory computer-readable media collectively having contents configured to cause a computing system to perform a method, the method comprising:
accessing a medical imaging image;
accessing a first machine learning model trained to recognize a view to which an image corresponds;
applying the first machine learning model to the accessed image to recognize a view to which the accessed image corresponds;
accessing a list of permitted anatomical features for images corresponding to the recognized view;
accessing a second machine learning model trained to identify any of a set of anatomical features visualized in an image;
applying the second machine learning model to the accessed image to identify any of the set of anatomical features visualized in the accessed image corresponds;
filtering the identified anatomical features to exclude any not on the accessed list; and
causing the accessed image to be displayed, overlaid with a visual indication of each of the filtered identified anatomical features.

5. The one or more instances of non-transitory computer-readable media of claim 4 wherein each overlaid visual indication of a filtered identified anatomical feature identifies at least one point within a visualization in the accessed image of the filtered identified anatomical feature.

6. The one or more instances of non-transitory computer-readable media of claim 4 wherein each overlaid visual indication of a filtered identified anatomical feature is a bounding box containing a visualization in the accessed image of the filtered identified anatomical feature.

7. The one or more instances of non-transitory computer-readable media of claim 4 wherein each overlaid visual indication of a filtered identified anatomical feature is a trace of a border of a visualization in the accessed image of the filtered identified anatomical feature.

8. The one or more instances of non-transitory computer-readable media of claim 4 wherein each overlaid visual indication of a filtered identified anatomical feature is a cover map overlay of a visualization in the accessed image of the filtered identified anatomical feature.

9. The one or more instances of non-transitory computer-readable media of claim 4 wherein each overlaid visual indication of a filtered identified anatomical feature is a name by which the filtered identified anatomical feature is known.

10. The one or more instances of non-transitory computer-readable media of claim 4 wherein the recognized view features a particular organ, and the permitted anatomical features listed for the recognized view comprise constituent structures of that organ.

11. The one or more instances of non-transitory computer-readable media of claim 4 wherein the recognized view features a particular organ, and the permitted anatomical features listed for the recognized view comprise landmarks of that organ.

12. The one or more instances of non-transitory computer-readable media of claim 4, the method further comprising:
training the first machine learning model; and
training the second machine learning model.

13. The one or more instances of non-transitory computer-readable media of claim 4 wherein the accessed medical imaging image is an ultrasound image.

14. A method in a computing system for training a machine learning model, the method comprising:
accessing a body of annotated ultrasound image training observations;
using at least a portion of the body of annotated training observations to train a first machine learning model to predict, based on an ultrasound image, a view it represents;
using at least a portion of the body of annotated training observations to train a second machine learning model to predict, based on an ultrasound image, anatomical structures it visualizes; and
persistently storing the trained first and second machine learning models, such that a production ultrasound image can be subjected to the first machine learning model to predict a view it represents, and can be subjected to the second machine learning model to predict anatomical structures it visualizes.

15. The method of claim 14, further comprising:
persistently storing, for each of a plurality of views represented by ultrasound images, indications of one or more anatomical structures that are expected to be visualizable in ultrasound images that represent the view, such that the anatomical structures that are predicted by subjecting the production ultrasound image to the second machine learning model can be filtered to exclude anatomical structures not indicated by the indications stored for the view that is predicted by subjecting the production ultrasound image to the first machine learning model.

16. The method of claim 14 wherein a portion of the second machine learning model is shared with the first machine learning model,
and wherein the second model is trained to obtain a trained state for the second machine learning model that includes a trained state for the shared portion of the second machine learning model,
and wherein, after the second model is trained, a portion of the first machine learning model not shared with the second machine learning model is trained, using the trained state of the portion of the second machine learning model shared with the first machine learning model.

17. The method of claim 14, further comprising expanding the body of annotated ultrasound image training observations after their annotation by duplicating the annotated ultrasound image training observations and modifying the duplicate ultrasound images in one or more ways that should not affect the view and structures predicted for them.

18. One or more instances of non-transitory computer-readable media collectively storing a data structure, the data structure comprising:
a machine learning model, the model comprising:
a first portion trained to predict, based on a radiological image, a view it represents; and
a second portion trained to predict, based on an radiological image, anatomical structures it visualizes,
such that the model can be applied to a distinguished radiological image to predict a view it represents and anatomical structures it visualizes.

19. The one or more instances of non-transitory computer-readable media of claim 18 wherein the radiological images based upon which the first and second portions of the model are trained to predict are ultrasound images.

20. The one or more instances of non-transitory computer-readable media of claim 18 wherein the first and second portions of the model are distinct.

21. The one or more instances of non-transitory computer-readable media of claim 18 wherein the first and second portions of the model intersect in a shared portion.

22. The one or more instances of non-transitory computer-readable media of claim 18 wherein each of the first and second portions of the model is comprised of one or more artificial neural networks.

23. The one or more instances of non-transitory computer-readable media of claim 18, the data structure further comprising:
for each of one or more views, a list of structures whose identification is permitted in radiological images that represent the view, such that the anatomical structures predicted to be visualized by the distinguished radiological image can be filtered to exclude any anatomical structures not on the list for the view the distinguished radiological image is predicted to represent.

24. The one or more instances of non-transitory computer-readable media of claim 18 wherein the second portion of the model takes as an independent variable a view, such that, when the second portion of the model is applied to the distinguished radiological image, it can also be applied to the view the distinguished radiological image is predicted by the first model to represent.

25. The one or more instances of non-transitory computer-readable media of claim 18 wherein the model contains a different second portion for each of a plurality of views, such that, when a second portion of the model is applied to the distinguished radiological image, a second portion for the view the distinguished radiological image is predicted by the first model to represent can be selected for application.

* * * * *